United States Patent
Vilsmeier et al.

(10) Patent No.: US 6,527,443 B1
(45) Date of Patent: Mar. 4, 2003

(54) PROCESS AND APPARATUS FOR IMAGE GUIDED TREATMENT WITH AN INTEGRATION OF X-RAY DETECTION AND NAVIGATION SYSTEM

(75) Inventors: Stefan Vilsmeier, Poing (DE); Rainer Birkenbach, Feldkirchen (DE)

(73) Assignee: BrainLAB AG, Heimstetten (DE)

( * ) Notice: Subject to any disclaimer, the term of this patent is extended or adjusted under 35 U.S.C. 154(b) by 0 days.

(21) Appl. No.: 09/387,597

(22) Filed: Aug. 31, 1999

(30) Foreign Application Priority Data

Apr. 20, 1999 (DE) ......................................... 198 17 867

(51) Int. Cl.[7] .............................................. A61B 17/00
(52) U.S. Cl. ...................................... 378/205; 378/206
(58) Field of Search ................................ 278/162, 164, 278/205, 206, 207, 63; 600/426, 427, 429

(56) References Cited

U.S. PATENT DOCUMENTS

| | | | |
|---|---|---|---|
| 3,720,817 A | 3/1973 | Dinwiddie | 235/151.11 |
| 4,118,631 A | 10/1978 | Froggatt | 250/492 R |
| 4,197,855 A | 4/1980 | Lewin | 128/653 |
| 4,341,220 A | 7/1982 | Perry | 128/630 |
| 4,360,028 A | 11/1982 | Barbier et al. | 128/659 |
| 4,583,538 A | 4/1986 | Onik et al. | 128/503 |
| 4,671,256 A | 6/1987 | Lemelson | 128/1.1 |
| 4,722,056 A | 1/1988 | Roberts et al. | |
| 4,791,934 A | 12/1988 | Brunnett | 128/653 |
| 4,945,914 A | 8/1990 | Allen | 128/653 |
| 5,222,499 A | 6/1993 | Allen et al. | 128/653.1 |
| 5,230,338 A | 7/1993 | Allen et al. | 128/653 |
| 5,315,630 A * | 5/1994 | Sturm et al. | 378/65 |
| 5,383,454 A | 1/1995 | Bucholz | |
| 5,389,101 A | 2/1995 | Heilbrun et al. | |
| 5,394,875 A | 3/1995 | Lewis et al. | 128/660.09 |
| 5,411,026 A | 5/1995 | Carol | |
| 5,590,215 A | 12/1996 | Allen | 382/128 |
| 5,603,318 A | 2/1997 | Heilbrun et al. | |
| 5,682,890 A | 11/1997 | Kormos et al. | 128/653.2 |
| 5,732,703 A | 3/1998 | Kalfas et al. | 128/653.1 |
| 5,769,789 A | 6/1998 | Wang et al. | 600/414 |
| 5,769,861 A | 6/1998 | Vilsmeier | 606/130 |
| 5,772,594 A | 6/1998 | Barrick | 600/407 |
| 5,799,055 A | 8/1998 | Peshkin et al. | 378/42 |
| 5,836,954 A | 11/1998 | Heilbrun et al. | |
| 5,851,183 A | 12/1998 | Bucholz | |
| 5,902,239 A | 5/1999 | Buurman | 600/427 |
| 5,967,982 A | 10/1999 | Barnett | 600/429 |
| 5,980,535 A | 11/1999 | Barnett et al. | 606/130 |
| 5,999,837 A | 12/1999 | Messner et al. | 600/407 |
| 6,050,724 A * | 4/2000 | Schmitz et al. | 378/205 |
| 6,122,541 A * | 9/2000 | Cosman et al. | 600/426 |
| 6,206,566 B1 * | 3/2001 | Schuetz | 378/205 |
| 6,223,068 B1 * | 4/2001 | Romeas et al. | 600/427 |

FOREIGN PATENT DOCUMENTS

WO  WO98/35720  8/1998

OTHER PUBLICATIONS

U.S. application No. 08/919,454, filed Aug. 28, 1997.

* cited by examiner

*Primary Examiner*—Robert H. Kim
*Assistant Examiner*—Hoon K. Song
(74) *Attorney, Agent, or Firm*—Renner, Otto, Boisselle & Sklar, LLP

(57) ABSTRACT

A process and apparatus for image-guided treatment of target areas, the process including the steps of: producing at least one x-ray image of a treatment area using an x-ray unit, the image including an x-ray image of a reference structure; mapping the reference structure three-dimensionally via a navigation system; and integrating the mapped data and the x-ray image in a computer unit having a display. The navigation system is capable of mapping operating instruments during surgery so that the mapped data of operating instruments can be output on the display in correct positional relationship with the x-ray image.

24 Claims, 2 Drawing Sheets

PROCESS AND APPARATUS FOR IMAGE GUIDED TREATMENT WITH AN INTEGRATION OF X-RAY DETECTION AND NAVIGATION SYSTEM

BACKGROUND OF THE INVENTION

1. Field of the Invention

The invention concerns a process and apparatus for image-guided treatment using an x-ray unit and a camera-assisted navigation system, i.e. image-assisted treatment of target areas with integrated radiographic mapping and navigation system.

2. Description of Prior Art

Known from German Patent DE 195 36 180 (corresponding to U.S. Pat. No. 5,769,861) are a process and apparatus for localizing an instrument, proposing the use of radiographic images in conjunction with a camera-assisted referencing system for instruments in stereotaxy or in orthopedic or neurosurgical operations. The disadvantage of the system proposed therein is the lack of teaching as to how such a link can best be exploited by the operating surgeon, i.e., a proposal is lacking as to how to suitably optimize the configuration of the interface between the operating surgeon and the technical system.

It is known furthermore to operate with the aid of continual radiographic mapping, i.e. using an x-ray unit, a radiation source and an image intensifier. An x-ray image is continually furnished which offers the operating surgeon a visual aid when displayed on a monitor. The disadvantage here is the continual exposure to high radiation, particularly as regards the hands of the surgeon. Moreover, only a relatively inaccurate imaging aid is provided which is usually only two-dimensional. When the x-ray unit is three-dimensionally referenced by camera-assisted (e.g. by LED's on an x-ray arm), the resulting mapping is subject to errors stemming from the relative instability of the x-ray unit. In C-arm x-ray units, the relative position of the source of radiation and the image intensifier often changes during operation.

SUMMARY OF THE INVENTION

It is, thus, the object of the present invention to provide a process and apparatus for image-guided treatment of target areas with integrated radiographic mapping and navigation system which obviates the aforementioned disadvantages of the prior art. In particular, there is provided a navigation system which only exposes the operating surgeon to low radiation while permitting precise mapping and wherein the interface between the surgeon and hardware is optimized.

To achieve these objects the invention provides a process for image-guided treatment of target areas comprising the steps of:
  producing at least one image of a treatment area by means of an x-ray unit while simultaneously imaging a reference structure;
  mapping the reference structure three-dimensionally via a camera-assisted navigation system; and
  marrying the mapping data of the target area, as determined from the x-ray image and the navigation system, in a single computer unit having a single display, so that the mapped data of operating instruments, as determined by the navigation system during surgery, is output on the display correctly assigned in position to the positions on the x-ray image.

The particular advantage of the solution in accordance with the invention is that the operating surgeon is now able to monitor his navigation by way of a single display output, on which the position of the surgical instruments married to the x-ray image is presented. In this arrangement, for two-dimensional navigation with the aid of the x-ray image it suffices in principle to make a single x-ray image at the start of the operation and to reference it in the camera-assisted navigation system via the reference structure, making sure that the patient is subjected to no further movement, and to operate by means of the camera-assisted navigation. This, of course, totally eliminates any radiation exposure of the surgeon's hands. The surgeon now sees the stored x-ray image on the display and simultaneously the position of his instruments with a very high accuracy which is now available from current navigation systems. Since the computer unit and display employed simultaneously processes the data made available by the x-ray image and by the camera-assisted navigation, the hardware requirement is reduced. When, a referencing means, trackable by the navigation system, is likewise applied to the patient, movement of the patient between navigation image and reference image is also permitted.

Once the x-ray image (reference image) has been made and assigned in the navigation system (navigation image), it is basically possible to again move the x-ray unit or even to remove it from the operating theater altogether since all data needed is namely stored in the computer unit. Accordingly, the integrated solution in accordance with the invention also has the advantage that now more space is available at the operating site.

When two, three, four or more x-ray images have been made in various locations in mapping the reference structure three-dimensionally, three-dimensional data may be made additionally available on the x-ray side, too.

In one preferred embodiment, several x-ray images of various, preferably overlapping, portions of the treatment area are made, and compiled into an overall view (landscape view), thus enabling, e.g., not only a single vertebra but also the complete spinal column to be imaged, the image being composed of inter linked single images.

Preferably, once a first x-ray image has been obtained, including the reference structure, and to which the mapping data has been assigned, a second x-ray image is produced in the same location without the reference structure, the second image then being displayed on the monitor. This prevents the x-ray image from being hindered by the reference structure, there being no impairment to accuracy as long as the relative locations of the x-ray unit and the patient are not changed.

As aforementioned, the x-ray images may be furnished as single images. However, in the case of highly complicated sections in the operation, intermediate images of a longer duration may be made to permit operating during radiation. All in all, however, the radiation exposure is significantly reduced for both patient and surgeon, since in simpler sections of the operation the x-ray source can be turned off.

Another advantage is that it is possible to use a body, transparent to x-rays, as the reference structure which is, more particularly in the shape of a truncated cone, comprising markers distributed characteristically imageable, and visible in the x-ray image.

For camera-assisted navigation, use is preferably made of a system comprising reflectors applied to the operating instruments and to the reference structure, for reflecting the radiation of a source of infrared radiation. It also is possible to employ a system having radiation emitters, more particularly LED's, applied to the operating instruments and to the reference structure.

The apparatus in accordance with the invention for image-guided treatment of target areas comprises:
  an x-ray unit with which at least one image of a treatment area is produced,
  a reference structure imaged simultaneously by the x-ray unit;
  a camera-assisted navigation system for mapping the three-dimensional location of the reference structure; as well as
  a single computer unit having a single display which marries the mapped data of the target area, as determined by the x-ray image and the navigation system, so that the mapped data of the surgical instruments, as determined by the navigation system during surgery, is output on the display correctly assigned in position to the positions on the x-ray image.

The x-ray unit used is preferably of the C-arm type with variable positioning.

In accordance with one embodiment of the invention, the reference structure is a body which is transparent to x-rays, more particularly in the shape of a truncated cone, comprising markers distributed characteristically imageable and visible in the x-ray image.

The camera-assisted navigation system is preferably a system comprising reflectors applied to the operating instruments and to the reference structure, for reflecting the radiation of a source of infrared radiation, however, possibly also being a system having radiation emitters, more particularly LED's, applied to the operating instruments and to the reference structure.

In one preferred embodiment, the x-ray unit comprises a radiation source and an image intensifier provided opposite thereto, the reference structure being secured, more particularly releasably secured, directly above the image intensifier of the x-ray unit. The reference structure is also mapped by the camera-assisted navigation system and its mapped data is sufficient for assigning the image data. Since it is only to the reference structure that reflectors or LED's need to be applied, referencing is now no longer dependent on the overall stability of the x-ray arm and thus precise results are obtained.

In another particularly preferred embodiment of the invention, both the computer unit and the display are configured as a unit integral with the x-ray unit, thus minimizing the space needed for accommodating the hardware, the unit including all its function elements being then transportable. Even the camera arrangement, may also be configured to this single unit.

BRIEF DESCRIPTION OF THE DRAWINGS

The invention will now be described in more detail by way of the embodiments with reference to the drawings in which.

DETAILED DESCRIPTION

Figure 1:
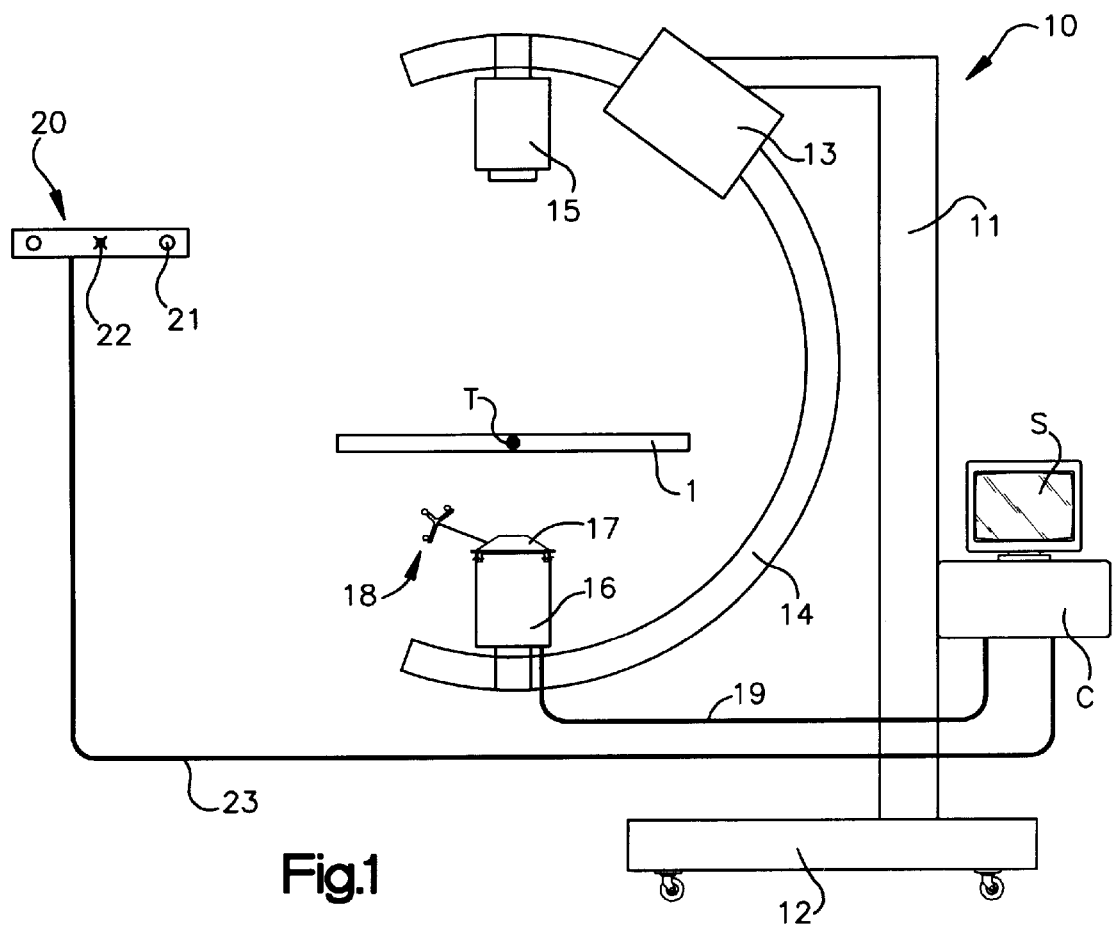
FIG. 1 is a basic representation of an apparatus in accordance with the invention comprising an x-ray unit and a camera-assisted navigation system.

FIG. 1 illustrates a simplified drawing of an apparatus in accordance with the invention including an x-ray unit and camera-assisted navigation system. It is the target area T in the schematically indicated body 1 of the patient that is intended for operation. For this purpose a C-arm x-ray unit 10 is used, standing on a castered and fixable base 12. Applied to the arm 11 is the guide 13 for the C-arm 14 which is held shiftingly or fixed in the guide 13. At its upper part, the C-arm holds a radiation source 15 and diametrically opposed thereto an image intensifier 16. The image signals of the image intensifier 16 are passed on by means of a cable 19 to the computer (C), which is likewise secured to the arm 11. The computer (C) includes a display (S).

Applied to the image intensifier 16 is a reference structure 17 via a mount, the mount being merely indicated in FIG. 1 without having a reference number allocated. The computer unit C furthermore receives mapped data from the camera unit 20 via the cable 23. The camera unit 20 comprises two infrared cameras 21 and a source 22 of infrared radiation, the camera unit being provided for direct mounting on the x-ray unit 10. By means of this camera unit the position of arrays of reflectors on adapters of the instruments used (operating instruments) is mapped and, thus, the position of the instruments themselves. As illustrated schematically in a simplified manner, the reference structure 17 also carries an adapter 18 so that its position can be mapped by the camera-assisted navigation system.

Figure 4:
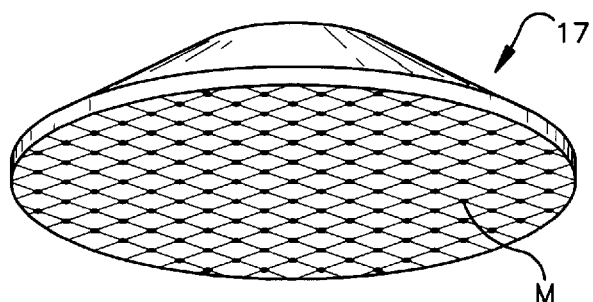
FIG. 4 is an interior view of a truncated cone reference structure with markers applied.

The reference structure 17 comprises furthermore markers M evident in the x-ray image, i.e., in the view of the truncated cone reference structure as seen from below, as shown in FIG. 4. These markers M are applied to the inner surface area of the truncated cone facing upwards in a pattern, the x-ray image data (projection) of which permits explicit position correlation by the computer unit C, whereby any additional distortions can be eliminated in computation. The markers M of the reference structure 17 are fully automatically recognized by the system, (searched for and marked in the x-ray image). The markers are preferably made of tungsten.

Figure 2:
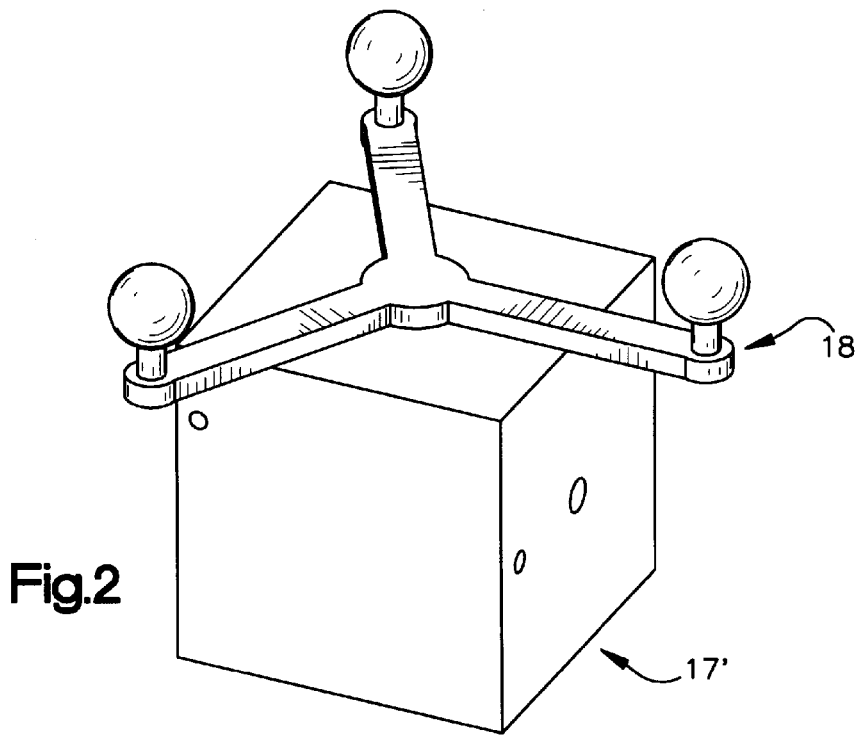
FIG. 2 is an illustration of one embodiment of a cubical reference structure including a reflector adapter.
Figure 3:
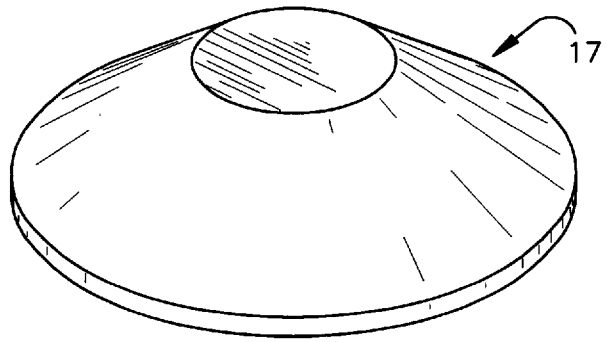
FIG. 3 is a three-dimensional basic illustration of a reference structure in the shape of a truncated cone.

From FIG. 3 a three-dimensional outward representation of the truncated cone reference structure 17 can be seen. Of course, the reference structure need not necessarily be in the shape of a truncated cone, it may also have the shape of a cube 17' comprising, likewise within its outer geometry, markers evident in the x-ray image. One such cube 17' is evident from FIG. 2 which also illustrates the application of the adapter with the reflector array (three spherical reflectors for infrared light). Furthermore, the reference structure need not necessarily be applied to the image intensifier 16, it could just as well be arranged anywhere between the source of radiation 15 and the image intensifier 16, e.g. also on the patient.

Figure 5:
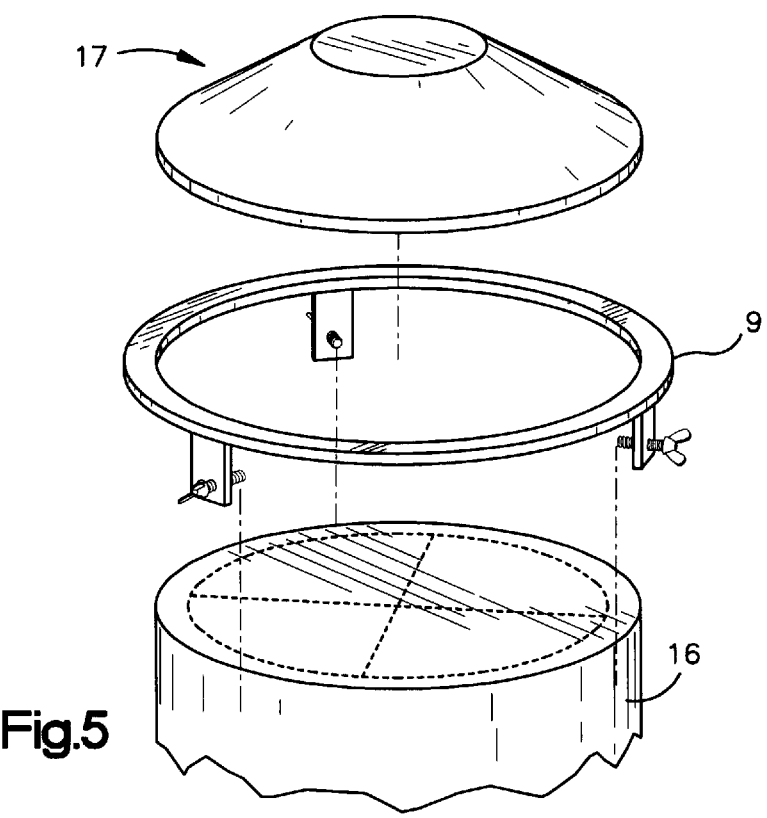
FIG. 5 is an exploded view of an arrangement for securing a reference structure to an image intensifier.

In FIG. 5 it is again schematically illustrated in an exploded view how a truncated cone reference structure 17 may be mounted on the upper part of the image intensifier by means of a mounting ring 9.

It is now possible for the operating surgeon to monitor his/her work by means of the described apparatus from a single display S indicating the positions of the operating instruments as married to the x-ray image. In this arrangement, once the patient 1 has been fixed in place, initially preferably two, three or four x-ray images are made in various positions of the C-arm 14, and the x-ray image data (including the marker pattern defining the position and three-dimensional location) are referenced and assigned by means of the reflector adapter 18 on the reference structure 17 in the camera-assisted navigation system. Each of the x-ray images may be duplicated, e.g., once with the reference structure applied to the image intensifier 16, and then with no change in position, with the structure removed so that use can be made of these images in the operation without being hindered by the structure 17, the structure 17 being needed, however, at least once in referencing each image.

It is then to be ensured that both the patient and x-ray unit 1 are no longer moved and that the operation is effectuated by means of camera-assisted navigation, i.e., with instruments which, likewise, due to the camera's position permit mapping and tracking. It should be noted in this case that the navigation systems suitable for this purpose are not only those operating actively or passively (as in the example embodiment) with infrared radiation, but also any other kind of tracking system, for instance, magnetic, acoustic, etc.

The exposure to radiation is greatly reduced. The surgeon sees the x-ray image on the display along with the position of his instruments with a very high accuracy which is now available from current navigation systems. Since the computer unit with display used for the operation simultaneously processes the data from the x-ray image and that of the camera-assisted navigation system, the hardware requirement is reduced and the unit is transportable as a whole.

What is claimed is:

1. A process for image-assisted treatment of target areas comprising the steps of:
   producing at least one radiographic projection image of a target area by means of an x-ray unit while simultaneously imaging a reference structure by means of the x-ray unit to create radiographic projection data;
   mapping the three-dimensional location of said reference structure via a navigation system to create mapped data;
   mapping the three-dimensional position of one or more operating instruments via the navigation system in the mapped data;
   marrying the mapped data of the reference structure as established by said navigation system with the radiographic projection data as established by said x-ray unit in a computer unit; and
   displaying the mapped data of said one or more operating instruments in correct positional relationship with the target area as determined from said radiographic projection image.

2. The process as set forth in claim 1, wherein producing at least one radiographic image includes producing at least two radiographic images in various locations for mapping said reference structure three-dimensionally.

3. The process as set forth in claim 1, wherein producing at least one radiographic image includes producing at least two radiographic images of various portions of said target area and compiling the at least two images into an overall view.

4. The process as set forth in claim 1, further comprising producing another radiographic projection image in the same location without said reference structure, wherein said second image is output on said display.

5. The process as set forth in claim 1, wherein producing said at least one radiographic projection image includes producing single images.

6. The process as set forth in claim 1, wherein producing said at least one radiographic projection image includes producing at least one image of longer duration.

7. The process as set forth in claim 1, wherein imaging said reference structure includes irradiating a body that is transparent to x-rays, said body supporting markers that are visible in said radiographic image.

8. The process as set forth in claim 1, wherein mapping the three-dimensional position of said one or more operating instruments includes reflecting radiation of a source of infrared radiation from reflectors applied to said operating instruments and to said reference structure.

9. The process as set forth in claim 1, wherein mapping the three-dimensional position of said one or more operating instruments includes emitting radiation from radiation emitters applied to said operating instruments and to said reference structure.

10. An apparatus for image-assisted treatment of target areas comprising:
    an x-ray unit for producing at least one radiographic projection image of a target area to create radiographic projection data;
    a reference structure imageable simultaneously with the target area by said x-ray unit, the location of the reference structure included in the radiographic projection data;
    a navigation system for mapping said three-dimensional location of said reference structure and for mapping the three-dimensional position of one or more operating instruments to create mapped data; and
    a computer unit with a display that is operable to marry the mapped data of the reference structure as determined by the navigation system with the projection image data of said target area as determined from the x-ray unit;
    wherein the display outputs the mapped data of the one or more operating instruments in correct positional relationship with the target area as determined from said radiographic projection image.

11. The apparatus as set forth in claim 10, wherein said x-ray unit is suitable for making two, three, four or more x-ray images in various positions, it more particularly being a C-arm x-ray unit with variable positioning.

12. The apparatus as set forth in claim 10, wherein said reference structure is a body transparent to x-rays, said body having more particularly the shape of a truncated cone, and the body comprising markers distributed characteristically which are visible in said x-ray image.

13. The apparatus as set forth in claim 10, wherein said navigation system includes reflectors applied to said operating instruments and to said reference structure, said reflectors reflecting the radiation of a source of infrared radiation.

14. The apparatus as set forth in claim 10, wherein said navigation system includes radiation emitters applied to said operating instruments and to said reference structure.

15. The apparatus as set forth in claim 10, wherein said x-ray unit comprises a radiation source and an image intensifier provided opposite thereto, said reference structure being secured directly above said image intensifier of said x-ray unit.

16. The apparatus as set forth in claim 10, wherein both said computer unit and said display are configured as a unit integral with said x-ray unit.

17. The process as set forth in claim 3, wherein producing includes producing several radiographic projection images of overlapping portions of said target area.

18. The process as set forth in claim 7, wherein irradiating said body includes irradiating a body having a truncated cone shape.

19. The process as set forth in claim 7, wherein irradiating said body includes irradiating markers having a characteristic arrangement.

20. The process as set forth in claim 9, wherein emitting radiation includes emitting radiation from light emitting diodes.

21. The apparatus as set forth in claim 14, wherein said radiation emitters are light emitting diodes.

22. The apparatus as set forth in claim 15, wherein said reference structure is releasably secured directly above said image intensifier of said x-ray unit.

23. The apparatus as set forth in claim 16, wherein said navigation system includes a camera arrangement, and said computer unit, said display and said camera arrangement are configured as a unit integral with said x-ray unit.

24. An apparatus for image-assisted treatment of target areas comprising:

an x-ray unit with which at least one x-ray projection image of a target area can be produced, a reference structure positioned within the field of view of the x-ray unit so as to appear in the x-ray image of the target area;

a navigation system that can map the three-dimensional location of the reference structure and the position of an operating instrument in the target area;

a computer unit that can integrate mapped data of the target area as established from the navigation system and x-ray projection image data of the target area as established by the x-ray unit to provide an integrated image of the target area, and that can integrate mapped data of the operating instrument as determined by the navigation system into the integrated image; and a display that can display the integrated image of the target area and the operating instrument.

\* \* \* \* \*